United States Patent [19]

Kimura et al.

[11] 3,933,733

[45] Jan. 20, 1976

[54] PHOSPHITE STABILIZED POLYVINYL CHLORIDE CONTAINING RESINS

[75] Inventors: Osamu Kimura, Toyonaka; Katsuhiro Mukai, Oita; Minoru Osada, Sagamihara; Shizuo Nara, Kamifukuoka; Yoshitaka Tanaka, Sagamihara; Masuo Yukitomi, Fuchu, all of Japan

[73] Assignees: Kyodo Chemical Company, Limited, Tokyo; Sumitomo Chemical Company, Limited, Osaka, both of Japan

[22] Filed: May 9, 1974

[21] Appl. No.: 468,586

Related U.S. Application Data

[63] Continuation-in-part of Ser. No. 307,634, Nov. 17, 1972, abandoned.

[30] Foreign Application Priority Data

Nov. 18, 1971 Japan.............................. 46-92524

[52] U.S. Cl.... 260/45.7 PH; 260/950; 260/DIG. 16
[51] Int. Cl.$^2$.............................................. C08K 5/52
[58] Field of Search............................. 260/45.7 PH

[56] References Cited
UNITED STATES PATENTS

| | | | |
|---|---|---|---|
| 2,938,877 | 5/1960 | Mack............................ | 260/45.7 PH |
| 3,009,939 | 11/1961 | Friedman..................... | 260/45.7 PH |
| 3,047,608 | 7/1962 | Friedman et al. ............ | 260/45.7 PH |
| 3,055,861 | 9/1962 | Hersh et al. ................. | 260/45.7 PH |
| 3,142,650 | 7/1964 | Friedman..................... | 260/45.7 PH |
| 3,305,520 | 2/1967 | Fritz et al. ................... | 260/45.7 PH |
| 3,644,578 | 2/1972 | Mathieu et al. ............. | 260/45.7 PH |
| 3,666,841 | 5/1972 | May et al..................... | 260/45.7 PH |

FOREIGN PATENTS OR APPLICATIONS

855,484 11/1960 United Kingdom ......... 260/45.7 PH

*Primary Examiner*—H. S. Cockeram
*Attorney, Agent, or Firm*—Wenderoth, Lind & Ponack

[57] ABSTRACT

Halogen-containing resins, particularly polyvinyl chloride, are stabilized by the incorporation of a phosphite of the formula,

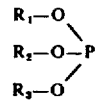

wherein one or two of groups $R_1$, $R_2$ or $R_3$ has the formula, $R(OC_nH_{2n})_m-$, in which R is an alkyl unsubstituted or substituted with at least one hydroxyl or chlorine, an alkenyl unsubstituted or substituted with at least one hydroxyl or chlorine, or an aralkyl, $n$ has a value of from 1 to 4, and $m$ has a value of from 1 to 8, and the remaining group $R_1$, $R_2$ and/or $R_3$ is an alkyl unsubstituted or substituted with at least one hydroxyl or chlorine, an alkenyl unsubstituted or substituted with at least one hydroxyl or chlorine, an aralkyl or an unsubstituted aryl.

7 Claims, No Drawings

PHOSPHITE STABILIZED POLYVINYL CHLORIDE CONTAINING RESINS

This application is a continuation-in-part of the co-pending application, Ser. No. 307,634, filed on Nov. 17, 1972 and now abandoned.

This invention relates to the stabilization of halogen-containing resins, particularly a polyvinyl chloride.

When a halogen-containing resin is processed, it will be exposed to a high temperature and therefore there will occur decomposition, dehydrochlorination and discoloration. It is already known that various stabilizers and stabilizing assistants are added to prevent such deterioration, as is described, for example, in British Patent No. 1,180,398.

It is also known to use these stabilizers and stabilizing assistants together to develop synergistic effects. Among such known stabilizing assistants are antioxidants, polyhydric alcohols and organic phosphites. However, these known stabilizers and stabilizing assistants are not fully satisfactory and are required to be improved. Further, the requirement for nontoxication is strong recently. In the case of nontoxic mixing without the use of Cd of Pb, there is no particularly satisfactory stabilizer today.

As a result of making hard investigations in view of these points, the present inventors have reached the present invention by finding that certain organic phosphites are very effective to this object.

Thus, the present invention is to provide a process for stabilizing a halogen-containing resin, which comprises incorporating from 0.01 to 10 parts by weight per 100 parts by weight of the said resin of a phosphite having the formula (I),

(I)

wherein one or two of groups, $R_1$, $R_2$ or $R_3$ has the formula, $R(OC_nH_{2n})_m-$, in which R is an alkyl unsubstituted or substituted with at least one hydroxyl or chlorine, an alkenyl unsubstituted or substituted with at least one hydroxyl or chlorine, or an aralkyl, $n$ has a value of from 1 to 4, and $m$ has a value of from 1 to 8, and the remaining group $R_1$, $R_2$ and/or $R_3$ is an alkyl unsubstituted or substituted with at least one hydroxyl or chlorine, an alkenyl unsubstituted or substituted with at least one hydroxyl or chlorine, an aralkyl or an unsubstituted aryl.

The phosphite of the present invention can be prepared by reacting a phosphite of the formula (II), $(R_4O)_3P$ (II)

wherein $R_4$ is an aryl or the same as R, with an alcohol of the formula (III), $R(OC_nH_{2n})_mOH$ (III)

wherein R, $m$ and $n$ are as defined above, in the presence of a basic catalyst.

In the present specification, the term "alkyl" is intended to mean an alkyl having 1 to 18 carbon atoms, the "aryl" is, for example, phenyl, tolyl, xylyl, tert-butylphenyl, octylphenyl, nonylphenyl, chlorophenyl, hydroxyphenyl, etc., the "aralkyl" is, for example, benzyl, phenethyl, etc. and the "alkenyl" is to mean an alkenyl having 2 to 24 carbon atoms, for example, oleyl, ricinoleyl, etc.

Examples of the alcohol are n-butoxyethanol, n-butoxydiethyleneoxyethanol, 2-ethylhexyloxy-propanol, nonyl-phenoxypropanol, lauryloxyethanol, oleyloxyethanol, ricinoleyloxyethanol, 2-benzyloxyethanol, butoxyethoxyethanol, etc.

The basic catalyst includes sodium hydroxide, potassium hydroxide, calcium hydroxide and lithium hydroxide.

In the present invention, favorable phosphites are represented by the formula,

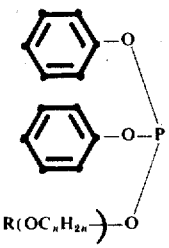

wherein R and $n$ are as defined above. The most favorable ones are 2-(2-butoxyethoxy)ethyl diphenyl phosphite which is a novel compound, 4-methoxybutyldiphenyl phosphite, 3-(2-ethylhexyloxy)propyldiphenyl phosphite, 2-benzyloxyethyldiphenyl phosphite and 2-isopropylbenzyloxyethyldiphenyl phosphite.

The reaction between triphenyl phosphite and said alcohol is conducted in the presence of said basic catalyst at a temperature of 80° to 180°C. The alcohol ($R_4OH$) by-produced may be removed during the reaction of after the completion of the reaction under a reduced pressure. The completion of the reaction can be confirmed by an amount of said phenol removed, and the reaction is usually conducted for 1 to 10 hours. Several typical examples of these phosphites and their refractive indexes at 25°C. and forms are shown in the following table.

However, the phosphites (I) of the present invention are not limited to these specific ones indicated in this table.

Table 1

| No. | Phosphite (I) | Refractive index | Form (25°C.) |
|---|---|---|---|
| 1 | 2-(n-butoxy)ethyldiphenyl phosphite | 1.5235 | Colorless transparent liquid |
| 2 | 4-methoxybutyldiphenyl phosphite | 1.5423 | " |
| 3 | 2-(n-butoxydiethylenoxy)-ethyldiphenyl phosphite | 1.5102 | " |
| 4 | 3-(2-ethylhexyloxy)propyldiphenyl phosphite | 1.5159 | " |
| 5 | 2-oleyloxyethyldiphenyl phosphite | 1.5342 | Light yellow transparent liquid |
| 6 | 2-ricinoleyloxyethyldiphenyl phosphite | 1.5716 | " |
| 7 | 2-benzyloxyethyldi- | 1.5005 | " |

Table 1-continued

| No. | Phosphite (I) | Refractive index | Form (25°C.) |
|---|---|---|---|
| 8 | phenyl phosphite<br>Octyl di(2-butoxyethyl)-phosphite | 1.4805 | Colorless transparent liquid |
| 9 | 2-(2-butoxyethoxy)ethyl-diphenyl phosphite | 1.5110 | " |
| 10 | 2-butoxyethyl p-chloro-phenyloleyl phosphite | 1.5030 | " |
| 11 | 2-isopropylbenzyloxy-ethyldiphenyl phosphite | 1.5000 | " |

The phosphites (I) of the present invention can be used together with any other generally known stabilizers, stabilizing assistants, antioxidants and ultraviolet ray absorbents.

Examples of these known stabilizers are carboxylates, mercaptides and mercaptates of Cd, Ba, Zn, Ca, Pb, Sn and $R_2Sn$ (R: alkyl).

Particularly, in the case of a nontoxic mixture used together with aliphatic acid salts of Ca—Zn, there will be given heat-resistance, transparency and coloring prevention much higher than in the case of using a known organic phosphite together with said salts. Further, in the case of using the stabilizer of this invention together with a Cd—Ba type stabilizer, particularly the weather-proofness of the resin will be greatly improved.

Examples of stabilizing assistants are epoxy compounds, other known organic phosphites and polyhydric alcohols.

Further, the phosphite (I) of the present invention serves also as a dropless agent which has the ability to prevent the formation of a water drop and drop flowing agent and also an antistatic agent. Particularly, even if this organic phosphite is used alone, it will be effective but, if it is used together with any other dropless agent or antistatic agent, it will develop a synergistically greater effect.

The organic phosphite of the present invention can also be used together with such additives for halogen-containing resins as, for example, a lubricant, filler and plasticizer.

The halogen-containing resin to be stabilized by the present invention may be polyvinyl chloride, a polymer blend of a polyvinyl chloride with any other blendable resin or a copolymer with vinyl chloride. The amount of the organic phosphite of the present invention to be added to a resin is 0.01 to 10 parts by weight, preferably 0.05 to 5 parts by weight per 100 parts by weight of the halogen-containing resin.

The present invention will be explained in more detail with reference to examples, which are only illustrative but not limitative. Parts are by weight.

EXAMPLE 1

248.2 g. (0.8 mol) of triphenyl phosphite and 131.2 g (0.81 mol) of 2-butoxyethoxyethanol were put into a flask of 500 ml. and 0.1 g. of sodium hydroxide was added thereto to react at 140°C. for 4 hours. The liberated phenol was distilled away by distillation under a reduced pressure (at 60°C. under 5 mm.Hg). Then the residual solution was filtered to obtain colorless transparent 2-(2-butoxyethoxy)ethyl diphenyl phosphite (Compound 9) as a filtrate.
Refractory index:   1.5110 (at 25°C.)
Specific gravity:   1.1910 (at 25°C.)
Other phosphites can be also produced in the same manner.

EXAMPLE 2

100 parts of a polyvinyl chloride resin (SX-11 produced by Sumitomo Chemical Company, Limited), 50 parts of dioctyl phthalate, 0.5 part of cadmium stearate, 0.5 part of barium stearate and 0.5 part of each of organic phosphites shown in Table 2 were mixed together and the mixture was kneaded on two rolls at 165°C. for 10 minutes to make a sheet. The thermostability of this sheet in a gear type deterioration tester, the press-test result (transparency and coloration) and weather resistance to the nature are shown in Table 2.

Table 2

| No. | Phosphite (Note 2) | | Thermostability tests | Press tests (Note 1) | | Weather resistance |
|---|---|---|---|---|---|---|
| | | | Time in minutes until it blackened in a gear oven at 180°C. | Transparency | Coloration | Number of months until discolored by exposure to nature |
| 1 | Not added | | 25 | 2 | 3 | 4 |
| 2 | Triphenyl phosphite (control) | | 35 | 1 | 2 | 6 |
| 3 | (2-ethylhexyl)di(phenyl) phosphite (control) | | 40 | 1 | 1 | 10 |
| 4 | Present invention compound | No. 1 | 50 | 1 | 1 | 14 |
| 5 | " | No. 9 | 55 | 1 | 1 | 14 |
| 6 | " | No. 3 | 50 | 1 | 1 | 14 |

Notes:
(1) The results of the press tests were indicated by showing the grades with the below mentioned numerals (here and hereinafter):
1: Very excellent
2: Excellent
3: Good
4: Rather bad
5: Not good
(2) The present invention compound numbers among the phosphites indicate the phosphites of the corresponding numbers in the above mentioned Table 1.

EXAMPLE 3

100 parts of a polyvinyl chloride resin (SX-11 produced by Sumitomo Chemical Company, Limited), 50 parts of dioctyl phthalate, 0.4 part of zinc stearate, 0.6 part of calcium stearate, 3 parts of epoxyated soybean oil and 1.0 part of each of organic phosphites in Table 3 were mixed together and the mixture was kneaded on two rolls at 165°C. for 10 minutes to make a sheet.

The thermostability of this sheet in a gear type deterioration tester and the results of press test (transparency and coloration) are shown in Table 3.

Table 3

| No. | Phosphite | Thermostability Time (minutes) until blackened in a gear oven at 180°C. | Press test Transparency | Press test Coloration |
|---|---|---|---|---|
| 1 | Not added | 20 | 3 | 3 |
| 2 | triphenyl phosphite (control) | 35 | 2 | 3 |
| 3 | Tri(nonyl phenyl) phosphite (control) | 40 | 3 | 2 |
| 4 | 2,4,6-trichlorophenyl bis(dipropylene glycol) phosphite (control, U.S.P. 3,333,026) | 25 | 3 | 3 (bleeding) |
| 5 | Tetrakis p-nonylphenyl propylene glycol diphosphite (control, British Pat. 1,180,398) | 45 | 3 | 2 |
| 6 | Present invention compound No. 2 | 55 | 2 | 1 |
| 7 | Present invention compound No. 4 | 60 | 2 | 1 |
| 8 | Present invention compound No. 7 | 60 | 1 | 1 |
| 9 | Present invention compound No. 8 | 60 | 2 | 1 |
| 10 | Present invention compound No. 9 | 60 | 2 | 1 |
| 11 | Present invention compound No. 11 | 60 | 1 | 1 |

EXAMPLE 4

100 parts of a polyvinyl chloride resin (SX-11 produced by Sumitomo Chemical Company, Limited), 50 parts of dioctyl phthalate, 1.5 parts of KV-39A-5 (produced by Kyodo Chemical Company Ltd.) as a stabilizer, 0.4 part of cadmium stearate, 0.2 part of barium stearate, 1.0 part of each of organic phosphites in Table 4, further 0.5 part of sorbitan distearate as a drop flowing agent and 0.5 part of sorbitan monopalmitate were mixed together and the mixture was kneaded on two rolls at 170°C. for 10 minutes to make a sheet.

The thermostability of this sheet in a gear type deterioration tester, the results of mealing test and the droplessness are shown in Table 4.

Table 4

| No. | Phosphite | Thermostability Time in minutes until blackened in a gear oven at 180°C. | Time in minutes until stuck with rolls at 170°C. | Droplessness |
|---|---|---|---|---|
| 1 | Not added | 50 | 45 | Water drops deposited |
| 2 | Triphenyl phosphite (control) | 60 | 50 | ″ |
| 3 | Present invention compound No. 6 | 75 | 65 | No water drop deposited |

EXAMPLE 5

100 parts of a polyvinyl chloride resin (SX-7G produced by Sumitomo Chemical Company, Limited), 10 parts of MBS (Kaneace B-12 produced by Kanegafuchi Chemical Co.), 4 parts of epoxidized soybean oil, 0.5 part of stearic acid, 1.0 part of a stabilizer KH-300A-6 (produced by Kyodo Chemical Company, Ltd.), 0.3 part of calcium stearate as a stabilizer, 0.3 part of zinc stearate and 0.5 part of each of organic phosphites in Table 5 where mixed together and the mixture was kneaded on two rolls at 180°C. for 5 minutes to make a sheet.

The results of mealing test of this sheet at 185°C. and the results of press test are shown in Table 5.

Table 5

| No. | Phosphite | Thermostability Colored degree after mealed with two rolls at 180°C. for 15 minutes | Time (minutes) until stuck with two rolls at 180°C. | Press test Transparency | Press test Coloration |
|---|---|---|---|---|---|
| 1 | Not added | 4 | 20 | 2 | 3 |
| 2 | Tri(nonylphenyl)phosphite (control) | 2 | 26 | 2 | 2 |
| 3 | Present invention compound No. 1 | 1 | 35 | 2 | 1 |
| 4 | Present invention compound No. 9 | 1 | 37 | 2 | 1 |
| 5 | Present invention compound No. 4 | 1 | 32 | 2 | 1 |
| 6 | Present invention compound No. 8 | 1 | 37 | 2 | 1 |

EXAMPLE 6

2.0 parts of each of organic phosphites in Table 6 were added to a paste sol consisting of 100 parts of a polyvinyl chloride resin (Sumilit PXNH produced by Sumitomo Chemical Company, Limited) and 60 parts of dioctyl phthalate and the heat-resistance and sol viscosity variation of the mixture were tested. The results are shown in Table 6.

As clear from this table, the phosphite of the present invention is very effective not only to the heat-resistance (discoloration prevention) but also to the prevention of the variation of the viscosity of the sol.

Table 6

| No. | Phosphite | Heat-resistance (Note 1) | | Sol viscosity variation (C.P.) | |
|---|---|---|---|---|---|
| | | Coloration occurred (min.) | Time (min.) until the blackening occurred | Just after | After 7 days |
| 1 | None (control) | 3 | 40 | 2,200 | 12,600 |
| 2 | Triphenyl phosphite (control) | 3 | 35 | 1,770 | 8,260 |
| 3 | Present invention compound No. 9 | 16 | 70 | 1,620 | 3,880 |

Note:
(1) The paste sol of the above mentioned mixture was well mixed with an ink roll, was debubbled in a vacuum and was flowed on a glass plate and its heat-resistance was tested in a gear oven at 180°C.

What is claimed is:

1. A composition consisting essentially of a polyvinyl chloride containing resin composition, stabilized with a stabilizing amount of a phosphite selected from the group consisting of 2-(n-butoxy)-ethyldiphenyl phosphite, 4-methoxybutyldiphenyl phosphite, 2-(n-butoxydiethylenoxy)ethyldiphenyl phosphite, 3-(2-ethylhexyloxy) propyldiphenyl phosphite, 2-oleyloxyethyldiphenyl phosphite, 2-ricinoleyloxyethyldiphenyl phosphite, 2-benzyloxyethyldiphenyl phosphite, octyl di(2-butoxyethyl)phosphite, 2-(2-butoxyethoxy)ethyldiphenyl phosphite, 2-butoxyethyl p-chlorophenyloleyl phosphite and 2-isopropylbenzyloxyethyldiphenyl phosphite.

2. The composition according to claim 1, wherein the phosphite is 2-(2-butoxyethoxy)ethyldiphenyl phosphite.

3. The composition according to claim 1, wherein the phosphite is 4-methoxybutyldiphenyl phosphite.

4. The composition according to claim 1, wherein the phosphite is 3-(2-ethylhexyloxy)propyldiphenyl phosphite.

5. The composition according to claim 1, wherein the phosphite is 2-benzyloxyethyldiphenyl phosphite.

6. The composition according to claim 1, wherein the phosphite is 2-isopropylbenzyloxyethyldiphenyl phosphite.

7. The composition according to claim 1, wherein the phosphite is used in an amount of 0.01 to 10 parts by weight per 100 parts by weight of said halogen-containing resin.

* * * * *